United States Patent [19]

Anifrani et al.

[11] Patent Number: 5,969,252
[45] Date of Patent: *Oct. 19, 1999

[54] PROCESS FOR THE PREDICTIVE DETERMINATION IN THE PRECRITICAL REGIME OF THE LOAD AT RUPTURE OF A STRUCTURE

[75] Inventors: Jean-Charles Anifrani, Saint Medard en Jalles; Christian Le Floc'h, Blanquefort, both of France

[73] Assignee: Aerospatiale Societe Nationale Industrielle, Paris Cedex, France

[*] Notice: This patent is subject to a terminal disclaimer.

[21] Appl. No.: 09/053,739

[22] Filed: Apr. 2, 1998

[30] Foreign Application Priority Data

Apr. 2, 1997 [FR] France .................................. 97-04300

[51] Int. Cl.⁶ .................................................. G01N 29/00
[52] U.S. Cl. .............................................. 73/587; 73/801
[58] Field of Search .............................. 73/587, 801, 810

[56] References Cited

U.S. PATENT DOCUMENTS

| | | | |
|---|---|---|---|
| 4,417,478 | 11/1983 | Jon et al. .................................... | 73/801 |
| 4,524,620 | 6/1985 | Wright et al. .............................. | 73/587 |
| 4,577,487 | 3/1986 | Dooley . | |
| 4,732,045 | 3/1988 | Blackburn . | |
| 5,014,556 | 5/1991 | Dunegan .................................... | 73/587 |
| 5,036,708 | 8/1991 | Urban et al. ............................... | 73/801 |
| 5,554,810 | 9/1996 | Anifrani et al. ........................... | 73/801 |

FOREIGN PATENT DOCUMENTS 0 665 432   8/1995   European Pat. Off. .

*Primary Examiner*—Max Noori
*Attorney, Agent, or Firm*—Young & Thompson

[57] ABSTRACT

A process for the predictive determination in the pre-critical range of the load at rupture of a structure, comprising subjecting the structure to a stress of the same type as the load and for a time according to a predetermined law, whilst recording the acoustical activity generated by the resulting damage, until a predetermined stress threshold is reached. A correlation is maintained between the registered acoustic emission and the relation $$\frac{dE}{dt} \sim \left(th\left[\frac{t_r - t}{\Delta}\right]\right)^{-\alpha} \left[1 + C\cos\frac{2\pi}{\log\lambda}\left(\log\left(th\left[\frac{t_r - t}{\Delta}\right]\right) + \phi\right)\right]$$

in which:

$$\frac{dE}{dt}$$

is the variation of acoustic energy generated by the damage, t is time, $t_r$ is the instant of rupture, $\Delta$, $\alpha$, C, $\lambda$ and $\phi$ are coefficients, so as to predetermine the value of prediction of the load at rupture from the above law connecting time and load.

6 Claims, 1 Drawing Sheet

PROCESS FOR THE PREDICTIVE DETERMINATION IN THE PRECRITICAL REGIME OF THE LOAD AT RUPTURE OF A STRUCTURE

FIELD OF THE INVENTION

The present invention relates to the prediction before rupture of the load at rupture of a structure.

BACKGROUND OF THE INVENTION

By structure is meant a finished material body, homogeneous or heterogeneous, designed to resist predetermined physical stresses which will be called "load", simple or combined, the invention seeking to predict the limit of resistance of said body relative to said charge.

Although the invention is susceptible to uses in many structures, it will be described as to its application for the inspection of storage reservoirs of gas under high pressure and more particularly still to the inspection of reservoirs made of composite material wound on a metallic liner.

Such reservoirs, generally spherical, adapted to resist internal pressures which can reach or exceed 800 bars, are subjected to non-destructive inspection among which is inspection by acoustic emission.

This technique, which seeks to inspect the soundness of the metal and of the composite material, consists in subjecting the reservoir to be tested to a predetermined applied pressure, which gives rise in the materials to microscopic irreversible damage whose appearance releases energy in thermal or acoustic form. Only the acoustical energy, which is more easily usable, is detected by the aid of piezoelectric detectors and permits detecting any incipient fault.

Thus, in the course of a test cycle by a monotone increasing from one pressure to a maximum predetermined pressure, typically the rated pressure, which is to say 1.5 times the service pressure of said reservoir, the acoustic emissions are recorded.

The use of these acoustic emissions permits, starting from preestablished criteria, certifying the reservoir to be safe or unsafe to fulfill its purpose.

It is evident that this technique, if it permits detecting or even localizing in the reservoir under test the faults, gives no indication of the effective value of the pressure at rupture, necessarily beyond the rated pressure.

Until now, there existed no inspection that quantifies for each reservoir the foreseeable level of pressure at rupture, which requires, for the sake of safety, using safety coefficients leading inevitably to overdimensioning. However, this overdimensioning gives rise in particular for structures of costly material, such as the reservoirs described above, for aeronautical or space use, to increases of weight and of undesirable cost.

So as to reduce this overdimensioning whilst increasing the safety of use of such structures, the applicant has already proposed in French FR-A-2 715 731, a non-destructive technique for the precise individual evaluation of each structure as to its effective limit of resistance to stresses which must be borne and in consideration of which it has been designed and produced.

In the field of pressure resistance of structures such as reservoirs of composite material wound on a metallic liner, one generally distinguishes three regimes in the course of increase of monotone pressure from zero to rupture of the structure, with the rupture pressure designated Pr.

Up to a value of pressure, very roughly fixed at 0.7 Pr, is located a so-called diffuse regime in which there is no display in the structure under test of interactions or correlations between eventual damage, such that no law can be established linking such damage, which renders impossible any prediction of the value Pr.

Beyond this first regime, and up to a value equal approximately to 0.95 Pr, there is a second regime called pre-critical, in which appear interactions between damage, having a spatial and temporal coherence. This is the beginning of a so-called cooperative process.

Finally, beyond the pre-critical regime and up to rupture of the structure, there is a third so-called critical regime, in which the interactions between damage are generalized and, by said cooperative process, lead to destruction of the structure.

In FR-A-2 715 731 there is described a process for the predictive determination of the load at rupture, using a power law taking account of the correlations between damage but essentially when these latter are in the totally cooperative process leading to rupture. Stated otherwise, the procedure cannot give really pertinent and reliable data as to the load at rupture of the structure under test except in the critical regime, which requires bringing the test pressure of the structure into the region near the rupture pressure.

However, this can give rise to a decrease in the rupture pressure Pr because of reaching a test pressure relatively near Pr is adapted to give rise to damage rendering the structure fragile, which is to say having consequences on the strength under pressure, thus lowering the value of Pr.

It is therefore desirable to reduce as much as possible the maximum test pressure for each structure.

SUMMARY OF THE INVENTION

It is particularly the object of the present invention to provide a process for the predictive determination of the load at rupture which will be both reliable and with a degree of optimum confidence and more precisely to provide a process using test pressures limited to the precritical range.

To this end, the invention has for its object a process for the predictive determination in the pre-critical range, of the load at rupture of a structure, in which said structure is submitted to stress of the same type as the load and depending on the time according to a predefined law, whilst recording the acoustic activity generated by the damages produced, to a predetermined stress threshold, characterized in that a correlation is effected between the acoustic emission recorded and the relation:

$$\frac{dE}{dt} \sim \left(th\left[\frac{t_r - t}{\Delta}\right]\right)^{-\alpha} \left[1 + C\cos\frac{2\pi}{\log\lambda}\left(\log\left(th\left[\frac{t_r - t}{\Delta}\right]\right) + \phi\right)\right]$$

in which:

$$\frac{dE}{dt}$$

is the variation of acoustic energy generated by said damage, t is time, $t_r$ is the instant of rupture, $\Delta$, $\alpha$, $C$, $\lambda$ and $\phi$ are coefficients, so as to determine the value of prediction of the load at rupture from the pre-established law connecting time to said load.

In its application to a structure constituted by a reservoir of a composite material wound on a metallic liner, the process is for example used by bringing the reservoir to an internal test pressure according to a predetermined protocol.

BRIEF DESCRIPTION OF THE DRAWINGS

There will now be described in greater detail the process of the invention with reference to the accompanying drawing in which the single figure represents the variation with time expressed as the number of blows of acoustic energy engendered during pressurization of a reservoir.

DETAILED DESCRIPTION OF THE INVENTION

Figure 1:
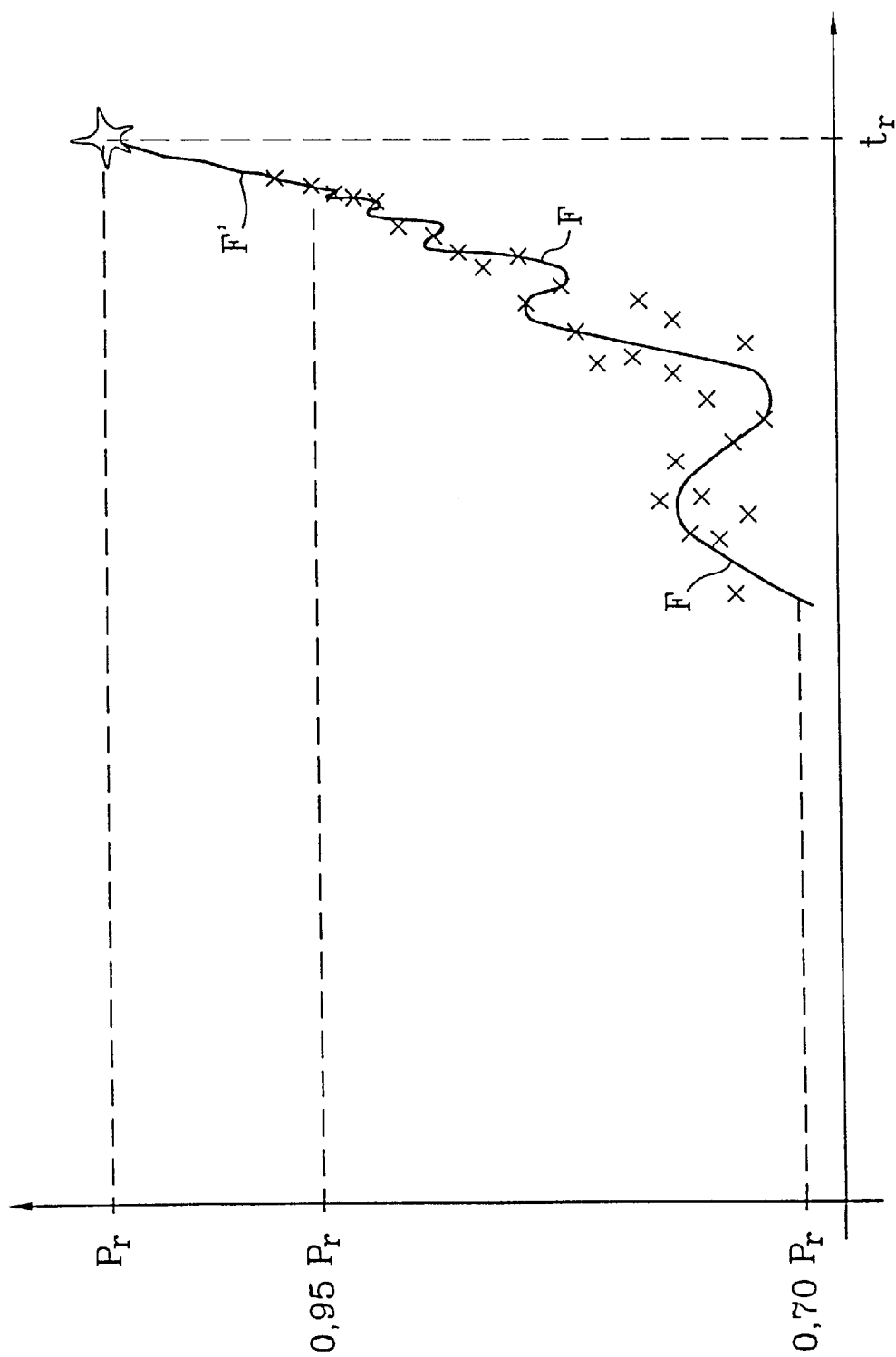

The process of the invention consists in subjecting for example a gas storage reservoir under high pressure which is to equip a satellite, of the type of composite material wound on a metallic liner, to an increase in load depending on the time, according to a predetermined law, whilst recording the acoustical activity generated by the damage caused, up to a threshold of predetermined pressure, lower than the rupture pressure.

The means for practicing the process are quite similar to those described in FR-A-2 715 731. The reservoir, for example spherical, is wound about at the level of its equator with a string of piezoelectric detectors connected to a recording device for the acoustical emission, comprising for example a system for acquisition of acoustical emission of the type LOCAN AT of the company EURO PHYSICAL ACOUSTICS.

The pressure increase protocol, the registration of the acoustical emission, the threshold of the events, the sum of the blows or accesses of the threshold of dissipated acoustic energy, are similar to those described in FR-A-2 715 731.

On the single figure, there has been shown the development as a function of time of the variation of energy $$\frac{dE}{dt}$$

engendered by acoustic emissions, said evolution being presented in the form of a layer obtained from the cumulative value of the number of blows of acoustic energy dissipated as a function of time progressively, of the process, leading to rupture, $t_r$ being the time of rupture of the reservoir.

The crosses represent exceeding the threshold or blows and are distributed in a more random pattern the farther one is from the point of rupture.

This randomness is only apparent because it has been able to be established according to the invention that the blows arrange themselves in an optimum manner according to the relation from the pre-critical regime:

$$\frac{dE}{dt} \sim \left(th\left[\frac{t_r - t}{\Delta}\right]\right)^{-\alpha} \left[1 + C\cos\frac{2\pi}{\log\lambda}\left(\log\left(th\left[\frac{t_r - t}{\Delta}\right]\right) + \phi\right)\right]$$

in which:

$$\frac{dE}{dt}$$

is the variation of acoustical energy generated by said damage, t is time, $t_r$ is the instant of rupture, $\Delta$, $\alpha$, C, $\lambda$ and $\phi$ are coefficients.

Then, by a process of adjustment between theory and experience called more precisely "fitting" between said blows and the above relation, there can be determined the six parameters of this latter, namely, $\Delta$, C, $\phi$, $\lambda$, $\alpha$ and $t_r$. The five first parameters are coefficients, the latter, $t_r$, permitting, from said pre-established law connecting the time of application of the load to the reservoir, predicting the load at rupture of this latter.

Among said coefficients, $\lambda$ is a positive integer of about 2, and $\phi$ is a dephasing coefficient.

In the drawing, there is represented at F the hyperbolic tangential function according to the relation given above, which "binds" as closely as possible the recorded blows.

It is to be noted that in the above relation, when $\Delta$ tends toward infinity, said relation transforms into a pure power law and more precisely the power law disclosed in FR-A-2 715 731. This is illustrated in the drawing by the substantially straight line portion F' of the curve F, which is the transition between the sinuous portion of the curve, taking into account the oscillatory character of the development of the blows, and the point of rupture.

The portion F' corresponds to the critical regime defined above, in the range comprised between 0.95 Pr and Pr, whilst the portion of the curve F below 0.95 Pr corresponds to the pre-critical regime.

The power law described in FR-A-2 715 731 therefore constitutes a limit case of that described in the present invention.

The principal interest of the present relationship using a hyperbolic tangential function appears clearly from the drawing. It suffices to conduct the pressure increase while remaining below the value 0.95 Pr, which is to say, to remain in the precritical regime, to gain sufficient information to determine the curve F.

The value of the prediction of Pr of the reservoir undergoing tests will thus be determined with a probability and an index of reliability as great as when using the relationship of FR-A-2 715 731, but while avoiding carrying the reservoir into the critical regime.

It remains true nevertheless that the closer the maximum test pressure approaches the value 0.95 Pr, the greater will be the reliability of the prediction and, conversely, it is not desirable to put too low a limit on the maximum test pressure.

In this connection, it will be seen that the coefficient $\Delta$, which is homogeneous with time, constitutes a criterion of determinative confidence in the sense that it fixes the extent of the field of predictivity beyond which uncertainty is too great, or even complete.

Thus $\Delta$ must preferably be greater than $t_r - t_p$, $t_p$ being the time of prediction, corresponding to stopping the increase of pressure of the reservoir undergoing tests.

If $\Delta$ is less than $t_r - t_p$, the "fitting" between the recordings of variations of acoustic energy and the hyperbolic tangential relation described above is too imprecise and hence leads to a prediction which is too uncertain.

It is therefore necessary for each test to verify the relationship $\Delta \geq t_r - t_p$. This latter relationship thus fixes the lower threshold of the maximum test pressure. This threshold, fixed by way of illustration at 0.70 Pr in the example in the drawing, constitutes the lower terminal of the precritical regime, but can however be quite variable according particularly to the conditions of manufacture of the reservoir.

Finally, the invention is applicable to any structure subjected to pressure, internal or external, and in a general manner to any structure submitted to stresses or mechanical loads, for example helicopter blades, sails, etc., it being understood that the stress for acoustical purposes that is applied according to the process of the invention is of the same nature as that for which the structure is designed.

It is to be noted to this end that the practice of the process of the invention does not require a knowledge of the shape, dimensions or characteristics of the materials of the structure and that it is precisely this universal character which permits the use of said process in other structures than reservoirs.

What is claimed is:

1. In a process for predictive determination in a pre-critical range of a load at rupture of a structure, comprising subjecting said structure to a stress equivalent to the load and for a time according to a predetermined law, whilst recording acoustical activity generated by resulting damage, until a predetermined stress threshold is reached; the improvement in which a correlation is maintained between registered acoustic emission and the relation $$\frac{dE}{dt} \sim \left(th\left[\frac{t_r - t}{\Delta}\right]\right)^{-\alpha}\left[1 + C\cos\frac{2\pi}{\log\lambda}\left(\log\left(th\left[\frac{t_r - t}{\Delta}\right]\right) + \phi\right)\right]$$

in which;

$$\frac{dE}{dt}$$

is the variation of acoustic energy generated by said damage, t is time, $t_r$ is the instant of rupture, $\Delta$, $\alpha$, $C$, $\lambda$ and $\phi$ are coefficients, so as to predetermine the value of prediction of the load at rupture from the above law connecting time and said load.

2. Process according to claim 1, wherein said coefficient $\Delta$ satisfies the relation $\Delta \geq t_r - t_p$, in which $t_p$ is the time at which the increase in stress is halted.

3. Process according to claim 1, applied to a reservoir of composite material wound on a liner, wherein the stress is a test pressure applied to the reservoir according to a predetermined protocol.

4. Process according to claim 3, wherein said test pressure is a monotone pressure increasing to said predetermined stress threshold.

5. Process according to claim 1, wherein said predetermined stress threshold is equal to 0.95 times the load at rupture.

6. Process according to claim 1, wherein the minimum threshold of applied stress is equal to 0.70 times the load at rupture.

* * * * *